US012766128B2

(12) United States Patent
Saad et al.

(10) Patent No.: US 12,766,128 B2
(45) Date of Patent: Oct. 20, 2026

(54) COMPOSITIONS AND METHODS FOR ANXIETY DISORDER TREATMENT

(71) Applicant: PSILOBRAIN THERAPEUTICS INC., Surrey (CA)

(72) Inventors: Fadia Saad, Victoria (CA); Rose Perry, Brooklyn, NY (US); Kevin Coft, Langley (CA)

(73) Assignee: Psilobrain Therapeutics Inc., Surrey (CA)

( * ) Notice: Subject to any disclaimer, the term of this patent is extended or adjusted under 35 U.S.C. 154(b) by 478 days.

(21) Appl. No.: 18/258,582

(22) PCT Filed: Dec. 21, 2021

(86) PCT No.: PCT/IB2021/062083
§ 371 (c)(1),
(2) Date: Jun. 21, 2023

(87) PCT Pub. No.: WO2022/137107
PCT Pub. Date: Jun. 30, 2022

(65) Prior Publication Data

US 2023/0372296 A1 Nov. 23, 2023

Related U.S. Application Data

(60) Provisional application No. 63/128,316, filed on Dec. 21, 2020.

(51) Int. Cl.

| | |
|---|---|
| ***A61K 31/4045*** | (2006.01) |
| ***A61K 9/00*** | (2006.01) |
| ***A61K 31/661*** | (2006.01) |
| ***A61K 31/7028*** | (2006.01) |
| ***A61P 25/22*** | (2006.01) |

(52) U.S. Cl.
CPC ........ *A61K 31/4045* (2013.01); *A61K 9/0053* (2013.01); *A61K 31/661* (2013.01); *A61K 31/7028* (2013.01); *A61P 25/22* (2018.01)

(58) Field of Classification Search
CPC .............. A61K 31/4045; A61K 9/0053; A61K 31/661; A61K 31/7028; A61P 25/22
See application file for complete search history.

(56) References Cited

U.S. PATENT DOCUMENTS

| | | | | |
|---|---|---|---|---|
| 2019/0099464 A1 | 4/2019 | Inarejos García | | |
| 2019/0142851 A1 | 5/2019 | Chadeayne | | |
| 2021/0322447 A1 * | 10/2021 | Plakogiannis | .......... | A61P 25/24 |

FOREIGN PATENT DOCUMENTS

| | | |
|---|---|---|
| WO | 2020212951 | 10/2020 |

OTHER PUBLICATIONS

Zhang, Lang, et al. "Crocin, a natural product attenuates lipopolysaccharide-induced anxiety and depressive-like behaviors through suppressing NF-kB and NLRP3 signaling pathway." Brain research bulletin 142 (2018): 352-359. (Year: 2018).*

Hibicke Meghan et al: "Psychedelics, but Not Ketamine, Produce Persistent Antidepressant-like Effects in a Rodent Experimental System for the Study of Depression", ACS Chemical Neuroscience, vol. 11, No. 6, Mar. 18, 2020 (Mar. 18, 2020), pp. 864-871.

Horsley Rachel R. et al: "Psilocin and ketamine microdosing: effects of subchronic intermittent microdoses in the elevated plus-maze in male Wistar rats", Behavioural Pharmacology, vol. 29, No. 6, Sep. 1, 2018 (Sep. 1, 2018), pp. 530-536.

Pitsikas N et al: "Effects of the active constituents of *Crocus sativus* L., *crocins*, in an animal model of anxiety", Phytomedicine, Elsevier, Amsterdam, NL, vol. 15, No. 12, Dec. 1, 2008 (Dec. 1, 2008), pp. 1135-1139.

* cited by examiner

*Primary Examiner* — Scarlett Y Goon
*Assistant Examiner* — David H Cho
(74) *Attorney, Agent, or Firm* — JMB Davis Ben-David

(57) ABSTRACT

Provided herein are compositions comprising an alkaloid compound of formula (I) having the structure: (I) wherein R1 is H or CH3, and R2 is H or PO3H2; or pharmaceutically acceptable salt thereof in combination with a therapeutically effective amount of crocin. Such compositions may be useful in treatment of anxiety disorder. Further provided herein are methods for treatment of anxiety disorder comprising administering to a patient in need thereof a therapeutically effective amount of an alkaloid compound having the structure: (I) wherein R1 is H or CH3, and R2 is H or PO3H2; or pharmaceutically acceptable salt thereof in combination with a therapeutically effective amount of crocin. Optionally, the amounts are synergistic and together provide an enhanced therapeutic effect.

13 Claims, 1 Drawing Sheet

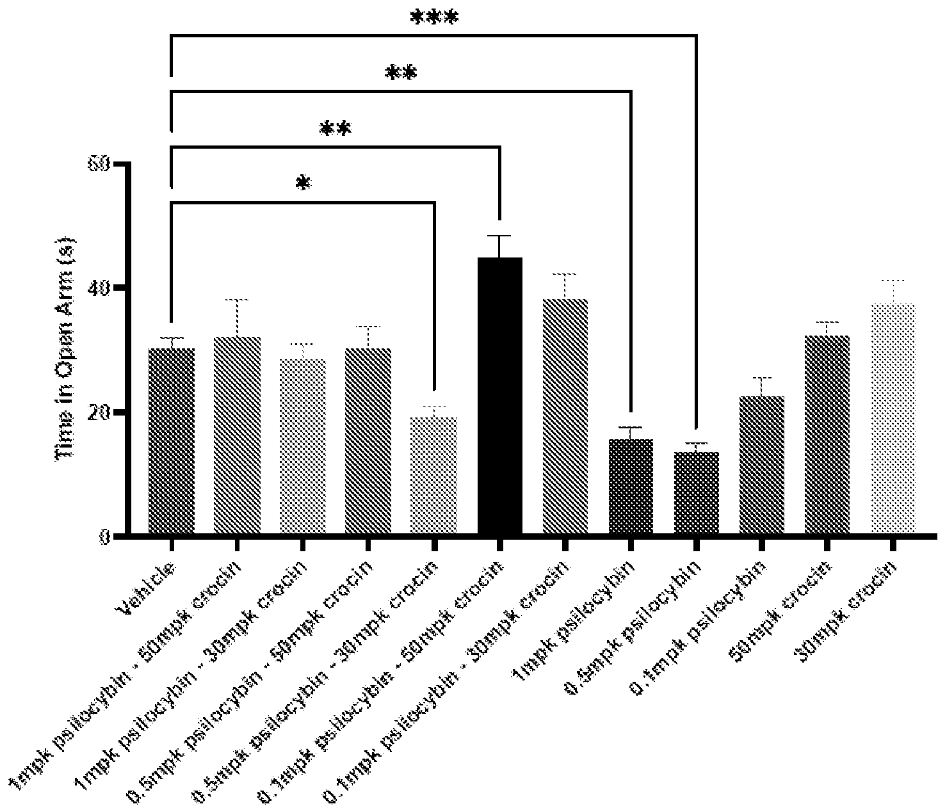
***
**
**
*
60
40
20
0
Time in Open Arm (s)
Vehicle
1mpk psilocybin - 50mpk crocin
1mpk psilocybin - 30mpk crocin
0.5mpk psilocybin - 50mpk crocin
0.5mpk psilocybin - 30mpk crocin
0.1mpk psilocybin - 50mpk crocin
0.1mpk psilocybin - 30mpk crocin
1mpk psilocybin
0.5mpk psilocybin
0.1mpk psilocybin
50mpk crocin
30mpk crocin

COMPOSITIONS AND METHODS FOR ANXIETY DISORDER TREATMENT

CROSS REFERENCE TO RELATED APPLICATIONS

This is the US National Stage of International Patent Application No. PCT/IB 2021/062083, filed on Dec. 21, 2021, which in turn claims the benefit to U.S. Provisional Patent Application No. 63/128,316 filed Dec. 21, 2020; the contents of which are both incorporated by reference herein in their entirety.

FIELD

This disclosure relates to treatments for anxiety disorder.

BACKGROUND

Anxiety disorder is a prevalent psychiatric disorder. Various types of anxiety disorder include: generalized anxiety disorder (GAD), specific phobias, and obsessive-compulsive disorder, and panic disorder. Post-traumatic stress disorder (PTSD) sufferers also often develop anxiety disorder.

Anxiety disorder can be experienced in patient having short spurts of anxiety known as panic attacks. Anxiety disorder may be associated with withdrawal from situations, changing in habits, feelings of dread, and restlessness. Physiological symptoms are sometimes induced by anxiety disorder, including headache, shortness of breath, chest pain and others.

Cognitive behavioral therapy is useful in some individuals for treatment of anxiety disorder, and pharmacological treatment is also used. Current pharmacological approaches to treating symptoms of anxiety disorder include but are not limited to: Agents acting on the g-aminobutyric acid (GABA) pathway such as benzodiazepines, agents that act on the serotonergic pathway such as selective serotonin re-uptake inhibitors (SSRIs) and serotonin norepinephrine reuptake inhibitors (SNRIs). However, benzodiazepines, SSRs and SNRIs have been associated with undesired effects including cognitive impairments, dependence and withdrawal, sexual malfunction and others.

SUMMARY

Provided herein are compositions comprising an alkaloid compound of formula (I) having the structure:

(I)

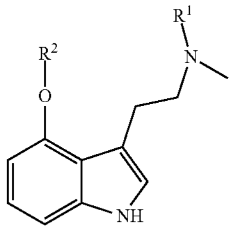

wherein $R^1$ is H or $CH_3$, and $R^2$ is H or $PO_3H_2$; or pharmaceutically acceptable salt thereof in combination with a therapeutically effective amount of crocin. Such compositions may be useful in treatment of anxiety disorder.

Further provided herein are methods for treatment of anxiety disorder comprising administering to a patient in need thereof a therapeutically effective amount of an alkaloid compound having the structure:

(I)

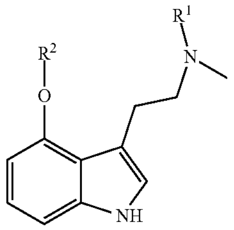

wherein $R^1$ is H or $CH_3$, and $R^2$ is H or $PO_3H_2$; or pharmaceutically acceptable salt thereof in combination with a therapeutically effective amount of crocin. Optionally, the amounts are synergistic and together provide an enhanced therapeutic effect.

The foregoing and other objects, features, and advantages will become more apparent from the following detailed description, which proceeds with reference to the accompanying figures.

BRIEF DESCRIPTION OF THE DRAWINGS

FIG. 1 is a bar graph showing average time spent of groups of mice in the open arm of an elevated plus maze model to represent anxiety disorder, after administration of psilocybin at various doses, crocin at various doses, or a combination of both psilocybin and crocin.

DETAILED DESCRIPTION

I. Terms

Unless otherwise explained, all technical and scientific terms used herein have the same meaning as commonly understood by one of ordinary skill in the art to which this disclosure belongs. The singular terms “a,” “an,” and “the” include plural referents unless context clearly indicates otherwise. Similarly, the word “or” is intended to include “and” unless the context clearly indicates otherwise. The term “comprises” means “includes.” The abbreviation, “e.g.” is derived from the Latin exempli gratia, and is used herein to indicate a non-limiting example. Thus, the abbreviation “e.g.” is synonymous with the term “for example.” In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art. Administration can be local or systemic. Examples of local administration include, but are not limited to, topical administration, intratumoral administration, subcutaneous administration, intramuscular administration, intrathecal administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs (such as the drug delivery devices described herein), which release the active agents and compounds over extended time intervals for sustained treatment effects. An implantable device is "implanted" by any means known to the art of insertion into the tissue or tissue environment that is the area of a given treatment.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Baeocystin: An alkaloid compound which has been found in the fungus *Psilocybe baeocystis* having the structure:

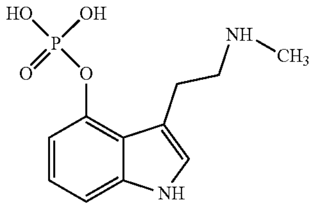 [SMILES: CNCCc1c[nH]c2cccc(OP(=O)(O)O)c12]

Botanical Drug Substance: A drug derived from one or more plants, algae, or fungi, prepared from raw materials by one or more than one of: pulverization, decoction, expression, extraction (water or ethanol) or similar processes. A botanical drug substance does not include a highly purified or chemically modified substance derived from natural sources.

Combination: A treatment modality combining two or more treatments (therapies or agents). Combination therapy may involve administration of the two or more treatments at the same time, sequentially, or with a gap of time between the administrations. In combination therapy, although not always administered simultaneously, the biological effects of both of the drugs or treatments occur on the subject at relatively the same time. Combination therapy may involve two (or more) drugs or treatments in one dosage form or multiple drugs or treatments in separate dosage forms.

Crocin: a compound found in crocus plants (*C. sativus*) stigma and styles and having the structure:

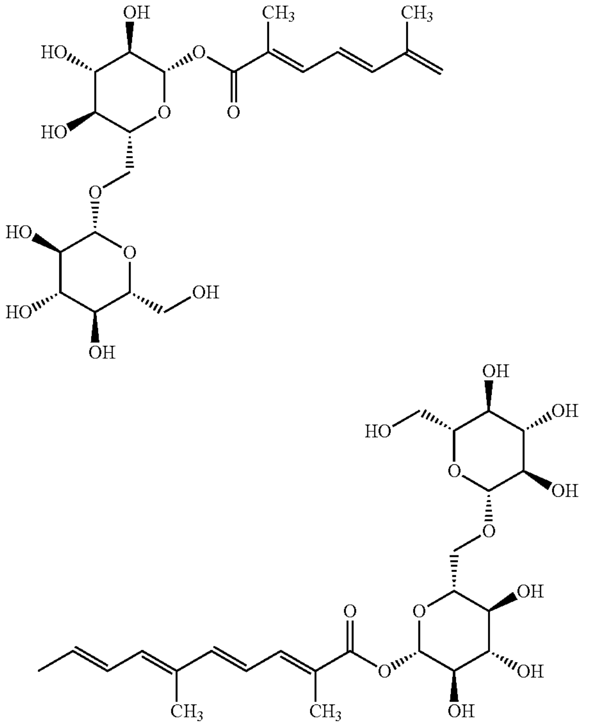

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity, and type of the affliction, and the manner of administration of the compound.

Pharmaceutically Acceptable Salt: The term "pharmaceutically acceptable salt" of a given compound refers to salts that retain the biological effectiveness and properties of the given compound, and which are not biologically or otherwise undesirable. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, methanesulfonic acid, ethanesulfonic acid, p-toluene-sulfonic acid, and the like.

Psilocin: An alkaloid compound which has been found in *Psilocybe baeocystis* having the structure:

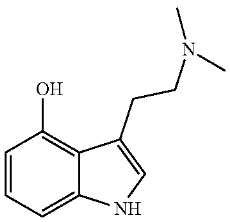

Psilocybin: An alkaloid compound which has been found in *Psilocybe baeocystis* having the structure:

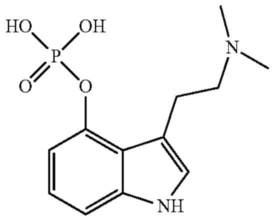 [SMILES: CN(C)CCc1c[nH]c2cccc(OP(=O)(O)O)c12]

Subject: Living multi-cellular organisms, including vertebrate organisms, a category that includes both human and non-human mammals.

Subject susceptible to a disease or condition: A subject capable of, prone to, or predisposed to developing a disease or condition. It is understood that a subject already having or showing symptoms of a disease or condition is considered "susceptible" since they have already developed it.

Synergy: refers to a clinical observation wherein a combination of two treatments, such as psilocybin therapy and crocin therapy, when administered in combination, provides more than additive effect of the individual therapies alone.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound.

II. Overview of Several Embodiments

Provided herein are compositions for use in treating anxiety disorder comprising a compound according to formula (I):

(I)

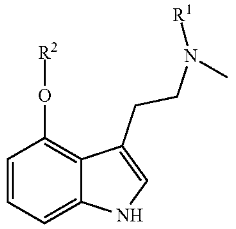

in combination with crocin.

According to an embodiment, the method comprises administering to the patient in need thereof, a compound according to formula (I), and crocin, once daily, twice daily, three times daily, or four times daily. The daily administration may continue for one day, two days, or three days. Optionally, administration may continue until a therapeutic effect is observed in the patient, for example, a reduction of a symptom of anxiety disorder. According to an embodiment, the method comprises administering to the patient in need thereof, a compound according to formula (I), and crocin, both through the oral route. According to an additional embodiment, the compound according to formula (I) and crocin are administered through the intravenous or intraperitoneal route.

According to an embodiment, a patient is administered a compound according to formula (I), and crocin as a combination therapy in two or more dosage forms, one comprising the compound according to formula (I) and the other crocin, or in one dosage form comprising both a compound according to formula (I) and crocin.

Pharmaceutical compositions comprising a compound according to formula (I), and crocin in a single dosage form and multiple dosage forms are disclosed herein. According to an embodiment, each of the compound according to formula (I), and crocin is present in the composition in a pharmaceutically effective amount. Optionally, the pharmaceutical composition comprises at least one pharmaceutically acceptable carrier. The carrier may be a suitable pharmaceutical diluent, excipient, or carrier.

According to an embodiment, the compound according to formula (I), and crocin are present in the pharmaceutical composition in an amount sufficient as to obtain a synergistic effect. A synergistic effect refers to a clinical observation wherein a combination of two treatments, such as a compound according to formula (I), and crocin therapy, when administered in combination, provides more than additive effect of the compound according to formula (I), and crocin alone.

According to an embodiment, the amount of compound according to formula (I) in the pharmaceutical composition corresponds to between 0.05-1 mg/kg, and the amount of crocin is 20-100 mg/kg.

According to an embodiment, methods for treatment of anxiety are disclosed herein, comprising administering to a patient in need thereof, a compound of formula (I) in an amount corresponding to 0.05-1 mg/kg of the patient per day, and the crocin in an amount corresponding to 20-100 mg/kg of the patient per day. For a 70 kg patient, this amount corresponds to 3.5 mg to 70 mg per day of compound of formula (I) and 1400 mg to 7 g per day of crocin.

The compound of formula (I) may be administered as an isolated compound, in a substantially purified form (over 95% or over 99%) after isolation from a psychedelic mushroom. Alternatively, the compound of formula (I) may be administered as part of a botanical drug substance, for example, as part of *Psilocybe* spp. Optionally, the botanical drug substance may further comprise other compounds including but not limited to aeruginascin or other indoleamine hallucinogenic compounds.

Crocin may be administered as an isolated compound in a substantially purified form (over 95% or over 99%) after isolation from a *Crocus sativus* plant. Alternatively, the crocin may be administered as part of a botanical drug substance, for example, as stigmas of the *Crocus sativus* flower.

According to an embodiment, the pharmaceutical composition is in the form of a solid dosage form or a liquid dosage form. The solid dosage form may be in the form of tablets, capsules, pills, powders, granules. The liquid dosage form may be in the form of tinctures, suspensions, syrups, and emulsions. The compositions may be formulated for administration through the following routes: intravenous (bolus or infusion), intraperitoneal, subcutaneous, or intramuscular.

When the pharmaceutical compositions are prepared in tablet form, they may further comprise: binders, lubricants, diluents, disintegrating agents, coloring agents, flavoring agents and/or flow-inducing agents. For oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compositions in liquid form can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

When the pharmaceutical compositions are prepared for parenteral administration, they may be in the form of a solutions, preferably containing a soluble salt of the active ingredient, suitable stabilizing agents, and if necessary, buffer substances. Sustained release liquid dosage forms suitable for parenteral administration, including, but not limited to, water-in-oil and oil-in-water microemulsions and biodegradable microsphere polymers, may be used according to methods well-known to those having ordinary skill in the art. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The dosage ranges are based upon our preclinical rodent studies testing the anti-anxiety effects of formula (I) and crocin (across varying doses and combinations) on mouse behavior in the elevated plus maze task (see FIG. 1). The elevated plus maze is one of the most widely used tests for measuring anxiety-like behavior and the anti-anxiety effects of pharmacological agents and is based on the natural aversion of mice for open and elevated areas, as well as their natural spontaneous exploratory activity in novel environments. Findings from our studies revealed that animals dosed with 0.1 mg/kg of a compound of formula (I), in particular, psilocybin, in combination with 50 mg/kg of crocin showed significantly increased time spent in the open arms of the maze relative to vehicle control mice, reflective of an anti-anxiety phenotype. When compound of formula (I) dosage levels were increased to 0.5 mg/kg and higher—either administered on its own or in combination with crocin—either no changes in mouse behavior were observed, or increased anxiety-like behavior as indicated by reduced time spent in the open arms of the maze was observed, relative to vehicle control mice. While the combination dose of 0.1 mg/kg of a compound of formula (I) with 50 mg/kg crocin produced the strongest anti-anxiety effects, 0.1 mg/kg of a compound of formula (I) with 30 mg/kg of crocin did not produce significantly different behavioral effects from this anxiolytic dose (0.1 mg/kg formula (I) with 50 mg/kg crocin), or from the 30 mg/kg crocin only or 50 mg/kg crocin only dosing groups. This suggests that synergistic anxiolytic effects of formula (I) and crocin can likely occur across a wide range of crocin (e.g., 20-100 mg/kg). Finally, these dosage ranges, as identified from our preclinical studies are commensurate with clinical dosages safely prescribed in humans.

According to some embodiments, described herein is a method for treatment of anxiety disorder in a patient in need thereof comprising administering to the patient a therapeutically effective amount of a compound of formula (I)

(I)

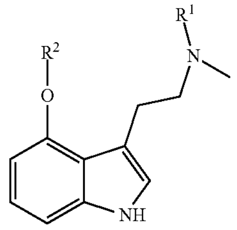

wherein $R^1$ is H or $CH_3$, and $R^2$ is H or $PO_3H_2$; or pharmaceutically acceptable salt thereof in combination with a therapeutically effective amount of crocin. Optionally, $R^1$ is $CH_3$, and $R^2$ is H. Optionally, $R^1$ is H, and $R^2$ is $PO_3H_2$. Optionally, $R^1$ is $CH_3$, and $R^2$ is $PO_3H_2$. Optionally, the compound according to formula (I) or the crocin is in the form of a botanical drug substance. Optionally, the compound according to formula (I) or the crocin is in isolated form. Optionally, the compound according to formula (I) and the crocin are each administered in an amount having a synergistic effect. Optionally, the therapeutically effective amount of the compound of formula (I) is 0.05-1 mg/kg of the patient per day. Optionally, the therapeutically effective amount of the crocin is 20-100 mg/kg of the patient per day. Optionally, the therapeutically effective amount of the compound of formula (I) is 0.05-0.3 mg/kg of the patient per day. Optionally, the therapeutically effective amount of the crocin is 30-60 mg/kg of the patient per day. Optionally, the compound of formula (I) or crocin are administered according to the oral route of administration. Optionally, both the compound of formula (I) and crocin are administered according to the oral route of administration. Optionally, the ratio of the compound of formula (I) to crocin, administered per day, by weight is between 1:20 to 1:2000, optionally, between 1:100 to 1:1200, or optionally, 1:500. Optionally, the compound of formula (I) and crocin are administered in a single dosage form.

Additionally described are combinations for use in treatment of anxiety disorder in a patient in need thereof comprising a therapeutically effective amount of a compound of formula (I)

(I)

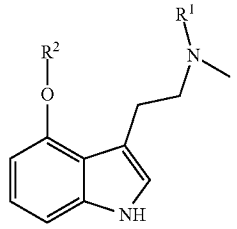

wherein $R^1$ is H or $CH_3$, and $R^2$ is H or $PO_3H_2$; or pharmaceutically acceptable salt thereof in combination with a therapeutically effective amount of crocin. Optionally, $R^1$ is $CH_3$, and $R^2$ is H. Optionally, $R^1$ is H, and $R^2$ is $PO_3H_2$. Optionally, wherein $R^1$ is $CH_3$, and $R^2$ is $PO_3H_2$. Optionally, the compound according to formula (I) or the crocin is in the form of a botanical drug substance. Optionally, the compound according to formula (I) or the crocin is in isolated form. Optionally, the compound according to formula (I) and the crocin are in an amount having a synergistic effect. Optionally, the therapeutically effective amount of the compound of formula (I) is 0.05-1 mg/kg of the patient per day. Optionally, the therapeutically effective amount of the crocin is 20-100 mg/kg of the patient per day. Optionally, the therapeutically effective amount of the compound of formula (I) is 0.05-0.3 mg/kg of the patient per day. Optionally, the therapeutically effective amount of the crocin is 30-60 mg/kg of the patient per day. Optionally, either the compound of formula (I) or crocin are administered according to the oral route of administration. Optionally, both the compound of formula (I) and crocin are administered according to the oral route of administration. Optionally, the ratio of the compound of formula (I) to crocin, administered per day, by weight is between 1:20 to 1:2000. Optionally, the ratio of the compound of formula (I) to crocin, administered per day, by weight is between 1:100 to 1:1200. Optionally, the ratio of the compound of formula (I) to crocin, administered per day, by weight is 1:500. Optionally, the compound of formula (I) and crocin are administered in a single dosage form.

The following examples are provided to illustrate certain particular features and/or embodiments. These examples should not be construed to limit the disclosure to the particular features or embodiments described.

EXAMPLES

Example 1: In Vivo Model of Anxiety Disorder

The elevated plus maze model is a behavioral assay for rodents which has been used to assess the anti-anxiolytic effect of pharmacological agents. In the model, anxiety behavior of rodents is assessed by determining the ratio of time spent on the arms relative to the time spent in the closed arms of the elevated plus maze structure. The model relies on rodents' affinity to dark, enclosed spaces.

In the elevated plus model, C57BL/6 mice, aged between 6 and 7 weeks were acclimated for at least five days and assigned randomly to treatment groups. Mice were housed on a 12 hour light/dark cycle. No more than 4 mice were kept in each ventilated cage. Mice were provided with standard rodent chow and water ad libitum. Test compounds were administered through the oral route in a volume of 10 milliliters per kilogram (ml/kg) and were formulated in 0.9% saline. 12 groups of mice were tested in the model, each group consisting of 10 mice. After acclimation, test compositions were administered to the animals in the amounts, in milligram per kilogram of mouse weight (mg/kg) according to table 1.

TABLE 1

| Group number | Dose of psilocybin (mg/kg) | Dose of crocin (mg/kg) |
|---|---|---|
| 1 | 0 | 0 |
| 2 | 1 | 50 |
| 3 | 1 | 30 |
| 4 | 0.5 | 50 |
| 5 | 0.5 | 30 |
| 6 | 0.1 | 50 |
| 7 | 0.1 | 30 |
| 8 | 1 | 0 |
| 9 | 0.5 | 0 |
| 10 | 0.1 | 0 |

TABLE 1-continued

| Group number | Dose of psilocybin (mg/kg) | Dose of crocin (mg/kg) |
|---|---|---|
| 11 | 0 | 50 |
| 12 | 0 | 30 |

As shown in the table, Group 1 was administered vehicle only. Groups 2 through 7 were administered various combinations of psilocybin and crocin. Groups 8-12 were administered either psilocybin alone or crocin alone. Behavioral testing was performed between 7-9 days after administration of the compounds.

Behavioral testing was performed as follows, at the beginning of the dark phase when animals were the most active. Testing was performed in dim light of 40 lux. The elevated plus maze consists of two open and two closed arms (arm length: 30 cm; width: 5 cm). Open arms have a small 1 cm edge and the closed arms are bordered by a 15 cm wall. At the beginning of the task, mice were placed in the center of the elevated plus maze facing an open arm. Mice were video tracked while exploring the maze for 5 min. The time spent in the open and closed arms was measured and analyzed.

The results in terms of average time in open arms, in seconds, is shown in FIG. 1. Comparisons were performed using 1 w-ANOVA, Fisher's LSD test. Significance is shown with a single asterisk if $P<0.05$, with a double asterisk if $P<0.01$, and with a triple asterisk if $P<0.001$.

Mice treated with 1 or 0.5 mg/kg showed a significant reduction in open arm time when compared to vehicle treated animals. When treated with the lowest dose of psilocybin, 0.1 mg/kg, there was no significant difference between the vehicle and the psilocybin treatment. This indicates that over the range of doses tested, psilocybin as a monotherapy appears not to have a beneficial effect, and at some dosages even has a detrimental effect on anxiety. Mice that were administered crocin alone as a monotherapy, in dosages of 50 or 30 mg/kg did not show a significant beneficial effect on anxiety relative to the mice in the vehicle group. However, when 0.1 mg/kg of psilocybin was used in combination with 50 mg/kg of crocin, a significant difference between vehicle and combination treatment was shown. When 0.1 mg/kg of psilocybin was used in combination with 30 mg/kg of crocin it appeared to provide a slight albeit not statistically significant anti-anxiolytic effect.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for treatment of anxiety disorder in a patient in need thereof comprising administering to the patient a therapeutically effective amount of a compound of formula (I)

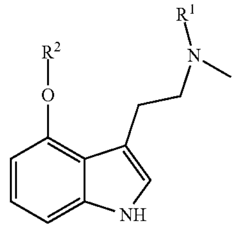

(I)

wherein $R^1$ is H or $CH_3$, and $R^2$ is H or $PO_3H_2$; or pharmaceutically acceptable salt thereof in combination with a therapeutically effective amount of crocin, wherein the compound according to formula (I) and the crocin are each administered in an amount having a synergistic effect, and wherein the weight ratio of compound according to formula (I) and the crocin is 1:500.

2. The method according to claim 1 wherein $R^1$ is $CH_3$, and $R^2$ is H.

3. The method according to claim 1 wherein $R^1$ is H, and $R^2$ is $PO_3H_2$.

4. The method according to claim 1 wherein $R^1$ is $CH_3$, and $R^2$ is $PO_3H_2$.

5. The method according to claim 1 wherein the compound according to formula (I) or the crocin is in the form of a botanical drug substance.

6. The method according to claim 1 wherein the compound according to formula (I) or the crocin is in isolated form.

7. The method according to claim 1, wherein the therapeutically effective amount of the compound of formula (I) is 0.05-1 mg/kg of the patient per day.

8. The method according to claim 7 wherein the therapeutically effective amount of the compound of formula (I) is 0.05-0.3 mg/kg of the patient per day.

9. The method according to claim 1, wherein the therapeutically effective amount of the crocin is 20-100 mg/kg of the patient per day.

10. The method according to claim 9 wherein the therapeutically effective amount of the crocin is 30-60 mg/kg of the patient per day.

11. The method according to claim 1 wherein either the compound of formula (I) or crocin are administered according to the oral route of administration.

12. The method according to claim 11 wherein both the compound of formula (I) and crocin are administered according to the oral route of administration.

13. The method according to claim 1 wherein the compound of formula (I) and crocin are administered in a single dosage form.

* * * * *